United States Patent [19]

Meyrat et al.

[11] Patent Number: 4,869,116
[45] Date of Patent: Sep. 26, 1989

[54] METHOD FOR APPARATUS FOR METERING LIQUID SAMPLES

[75] Inventors: Pierre-André Meyrat; Alain Oppliger, both La Chaux-de-Fonds; Denis Steiner, St-Imier, all of Switzerland

[73] Assignee: Nivarox-FAR S.A., Le Locle, Switzerland

[21] Appl. No.: 136,888

[22] Filed: Dec. 22, 1987

[30] Foreign Application Priority Data

Dec. 24, 1986 [FR] France ................................ 86 18256

[51] Int. Cl.[4] .............................................. G01N 1/14
[52] U.S. Cl. .................................................. 73/864.34
[58] Field of Search ........... 73/863.01, 863.23, 863.24, 73/863.25, 864.21, 864.31, 864.23, 864.34, 864.35, 863.83, 863.84, 864.81, 863.73, 864.01; 422/100, 68, 81, 82; 222/249, 55, 95, 163, 168.5

[56] References Cited

U.S. PATENT DOCUMENTS

| 3,369,346 | 2/1968 | Wildbolz et al. | 73/863.25 |
| 3,795,149 | 3/1974 | Gillette et al. | 73/863.24 |
| 3,986,401 | 10/1976 | Peterson | 73/864.35 |
| 4,037,464 | 7/1977 | Wenander | 422/100 |
| 4,457,184 | 7/1984 | Shiono | 73/864.11 |
| 4,478,095 | 10/1984 | Bradley et al. | 73/864.23 |
| 4,483,825 | 11/1984 | Fatches | 73/864.01 |
| 4,693,984 | 9/1987 | Minton et al. | 422/100 |

FOREIGN PATENT DOCUMENTS

| 8502019 | 5/1985 | European Pat. Off. . | |
| 0185330 | 6/1986 | European Pat. Off. . | |
| 2489515 | 3/1982 | France . | |
| 878504 | 10/1961 | United Kingdom | 73/864.35 |
| 1533661 | 11/1978 | United Kingdom | 422/81 |
| 2069974 | 9/1981 | United Kingdom | 73/864.23 |

Primary Examiner—Stewart J. Levy
Assistant Examiner—Robert R. Raevis
Attorney, Agent, or Firm—Sughrue, Mion, Zinn, Macpeak & Seas

[57] ABSTRACT

First and second containers (R1; R2) are successively brought to a transvasation or decanting station (C) in which the samples are metered. For this purpose, a piston (17) is mounted so as to be able to penetrate each first container (R1), which can be lifted, when it enters the decanting station (C). The quantity of sample in the first container (R1) is greater than the quantity to be precisely metered which is poured into the second container (R2) by means of a pouring assembly (24 to 36) situated above it. A pouring member (40) may be placed between the second container and the pouring assembly. Thus, when the first container acts as cylinder on the piston (17), a first quantity of the sample rinses the transvasation or decanting circuit to eliminate any residue of a preceding sample, while the pouring member is located between the pouring assembly (24 to 36) and the second container, then an exactly metered quantity of the sample is poured into the second container after withdrawal of the pouring member (40).

10 Claims, 8 Drawing Sheets

METHOD FOR APPARATUS FOR METERING LIQUID SAMPLES

BACKGROUND OF INVENTION

This invention relates to a method of and apparatus for metering liquid samples.

When it is desired to successively process a large number of liquid samples with precise volumetric metering, the parts involved in the metering operation and the passageways communicating with these parts need to be rinsed.

Generally, the cleaning of the flow circuit for the samples is carried out with a rinsing liquid which washes this circuit after the metering of successive samples so as to remove any residues from the previously processed sample.

Unless this precaution is taken, such residues may modify the characteristics of the following sample such as its composition or its concentration, which could result in errors in the analysis.

Apart from the risk that the rinsing operation may modify the concentration of the samples, since there is always a residual quantity of rinsing liquid in the flow circuit, it must also be noted that specific members are needed to perform this operation and the time needed to handle each sample is increased because during cleaning no metering can be carried out.

In an earlier more elaborate proposal for carrying out the general idea set out above (see US-A-4 457 184), there is described a method of collecting samples in which a pipette is rinsed with a rinsing liquid, a given quantity of air is then sucked into the pipette, whereupon a given quantity of sample is sucked in. The sample is thus separated from the rinsing liquid by an air bubble. This technique is delicate and always requires a rinsing liquid.

SUMMARY OF INVENTION

The object of the invention is to provide a method and apparatus by means of which the metering of successive samples may be carried out without a rinsing liquid and without upsetting either the composition or the concentration of the samples, and also without increasing the time for processing each sample over and above the length of time needed for metering.

The method according to the invention comprises preparing, in a plurality of first containers, samples whose volume is made up of a given quantity of a sample to be obtained plus an excess quantity of sample, and successively transvasing or decanting the contents of each of said first containers firstly towards an evacuation means up to a maximum quantity corresponding to said excess quantity, then towards a second container up to said given quantity of sample to be obtained.

By proceeding in this way, the excess quantity of the following sample is used to rinse the sample flow circuit, by driving out of the circuit any residue of the preceding sample, whereupon the second containers will receive only a correct quantity of sample consisting exclusively of the liquid formed by the following sample.

The apparatus provided by the invention, for carrying out the above-defined method, comprises a plurality of pairs of first and second containers, the first containers each being adapted to contain a sample to be metered plus a quantity in excess of the volume to be obtained, the second containers being adapted to receive the metered volumes of the sample, a station for transvasing or decanting successive samples from their first container into their second container this transvasation or decanting station comprising means for pumping sample to carry out the decanting, a pouring assembly adapted to communicate with the second containers and selective discharge means adapted to be selectively positioned between the pouring assembly and each second container during a predetermined period of time at the beginning of the transvasation decanting operation and to be withdrawn during the remainder of the decanting operation, said predetermined period of time corresponding at most to the decanting of the excess quantity of the sample, and transport means for successively bringing each pair of first and second containers into the decanting station.

BRIEF DESCRIPTION OF DRAWINGS

The invention will be better understood from the following description which is solely by way of example and made with reference to the accompanying drawings, in which.

DETAILED DESCRIPTION

In the following, the invention will be described in relation to its application to analysing apparatus able automatically to measure the amount of ATP (adenosine triphosphate) in a medium such as soil so as to estimate the biological activity of the medium.

In an article in the publication "Soil Biol. Biochem." vol. 16, no. 4, pp 361–366, 1984, N. Maire describes a method of analysing a medium, such as soil, which consists first in extracting the ATP molecule from the medium's cells by rupturing the cell's walls and then in photometrically measuring the molecule by an enzymatic bioluminescence reaction. This is made possible because the intensity of the light emitted during this reaction is directly proportional to the concentration of ATP and because this concentration is representative of the biological activity of the soil sample under examination, ATP being a mononucleotide of the metabolism that is found in all living organisms and which ensures the transmission or the storage of energy in most biochemical reactions taking place in living cells (respiration, fermentation, photosynthesis, etc.).

Extraction of the ATP molecule by rupturing the cell walls is carried out by diluting the soil sample in a given quantity of acid such as $H_2SO_4$, preferably completed by a mechanical mixing operation of the thus-diluted sample. Because the enzymatic reaction required for the photometric analysis cannot take place in an acid medium, it is necessary, before proceeding with the photometric analysis, to adjust the pH to a practically neutral value by the addition of an adjuvant for this purpose. The pH adjustment must of course be carried out on a well determined volume of the sample and it is in this respect that the essential features of the invention come into play in the apparatus described below.

Of course, the following description of this analysing apparatus must not be considered as a limitation of the applications of the invention which, on the contrary, may be used whenever it is desired to meter a given number of individual samples without a risk of contamination between the samples.

Figure 1:
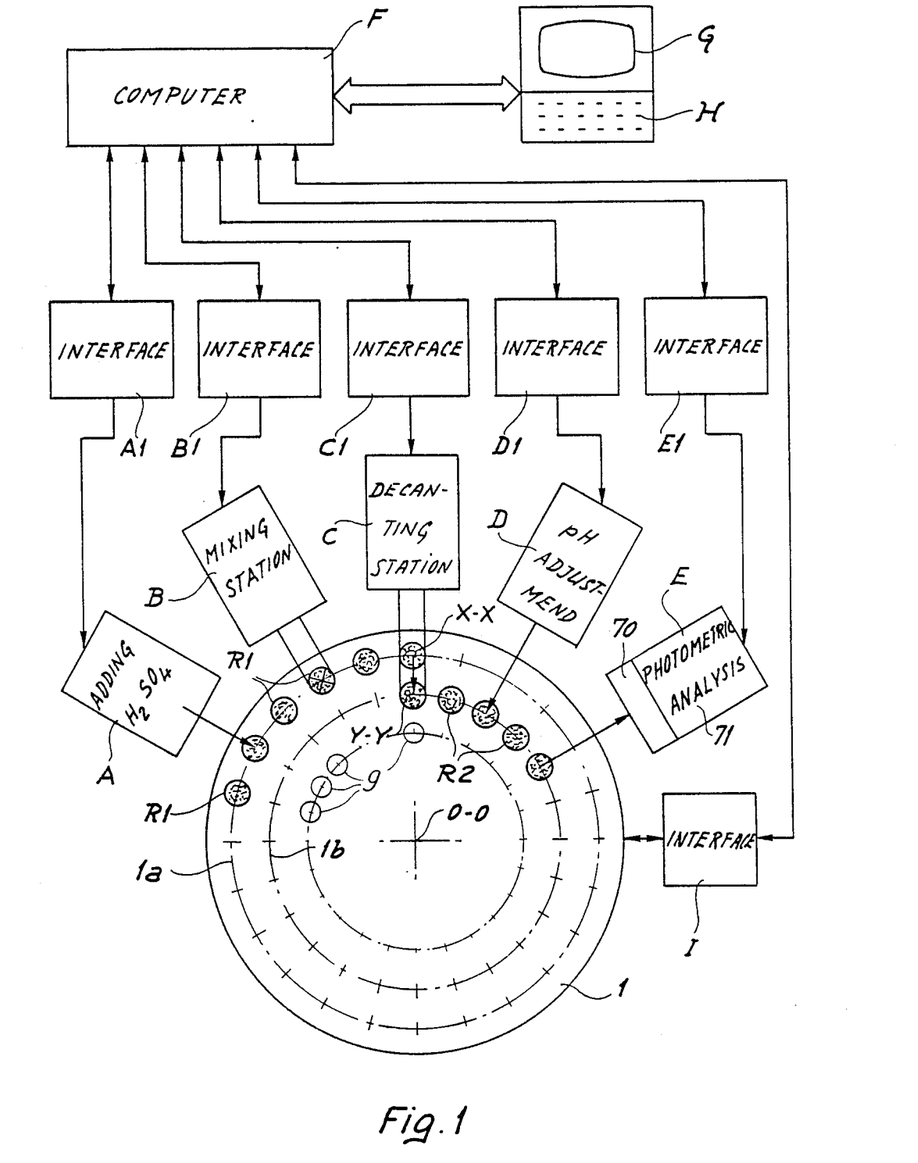
FIG. 1 is a schematic diagram of analysis apparatus for carrying out the method according to the invention.

In the diagram of FIG. 1, there is shown a plate or carrier 1 mounted rotatably about a vertical axis 0—0. On a first 1a of this carrier are arranged first containers R1 and, on a second circle 1b which is concentric with but of smaller diameter than the first circle, are arranged second containers R2. The containers are shown filled with liquid.

About the carrier 1 are grouped several work stations designated by the letters A to E and which successively perform on the samples the following operations:

Station A—addition of a given quantity of $H_2SO_4$ to the solid sample previously put in the containers R1.

Station B—mixing of the solution obtained at station A.

Station C—transvasation or decanting of the sample for simultaneous metering and filtering (method according to the invention).

Station D—adjustment of the pH.

Station E—photometric analysis of the sample issuing from the station D.

Stations A to E are controlled via corresponding interfaces A1 to E1 which convert the orders of a computer F into control signals usable by the various members of the work stations A to E. The computer F is equipped with a viewing screen G and a control keyboard H. The apparatus operates automatically in acordance with a program carried out in the computer F.

The carrier 1 moves with an intermittent rotational movement also controlled by the computer F via an interface I.

It is to be noted that, before they are placed on the carrier 1, the solid samples prepared in the containers R1 are preferably made up according to the teachings of U.S. patent application Ser. No. 083344 filed August 10, 1987 and entitled "Method of manufacture of an element including a predetermined quantity of a given substance and the element resulting from such method".

FIGS. 2 to 5, which show the transvasation or decanting station C enabling accurately metered samples to be obtained for analysis, will now be described.

Figure 2:
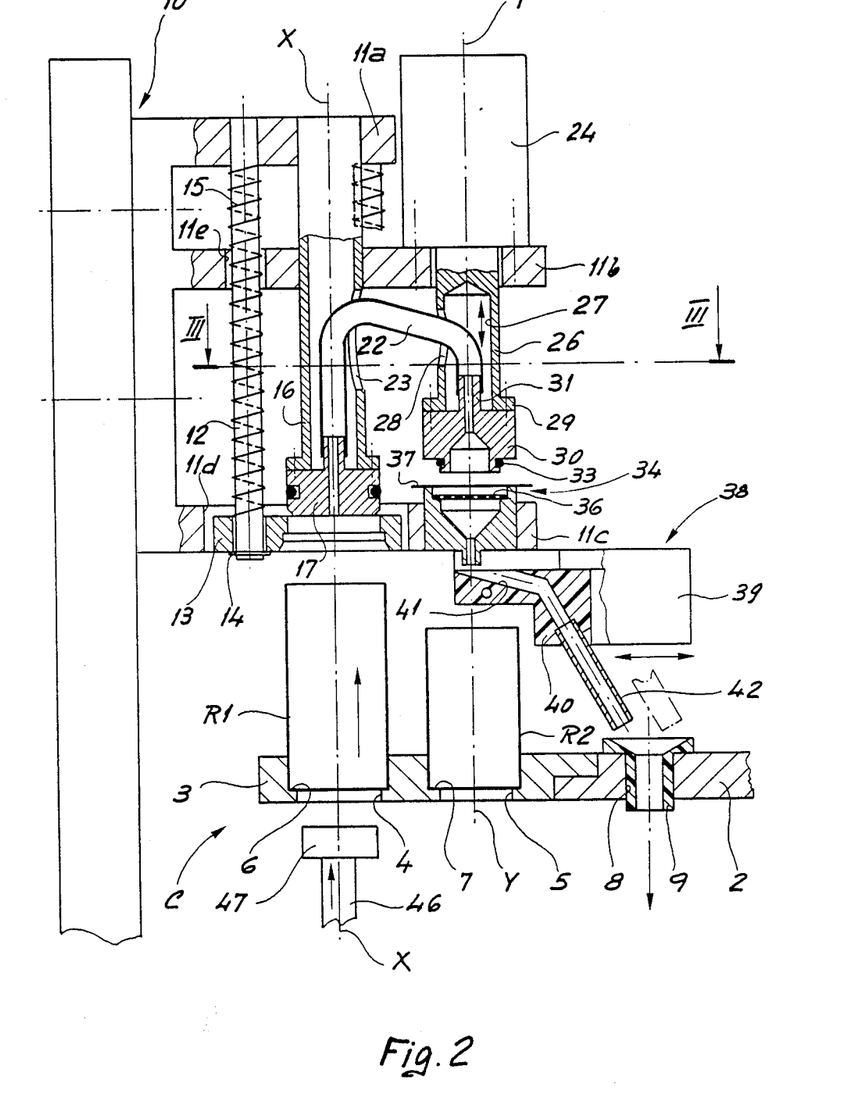
FIG. 2 is a side elevational view, partially in cross-section along line II—II of FIG. 3, of a transvasation/metering station used in the apparatus of FIG. 1.
Figures 3, 7:
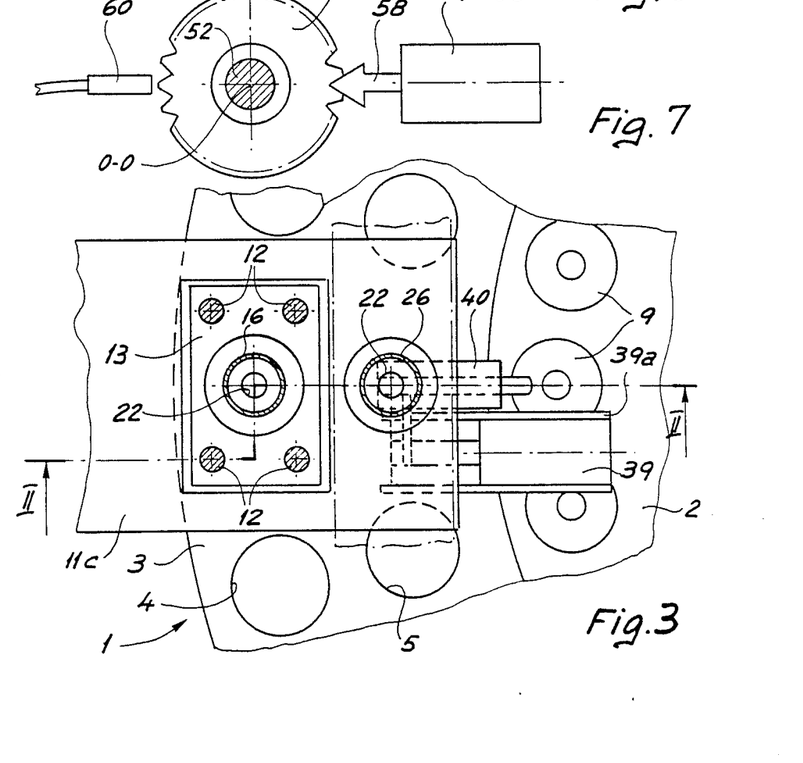
FIG. 3 is a horizontal cross-section along line III—III of FIG. 2.
FIG. 7 is a view along line VII—VII of FIG. 6 showing a device for indexing the position of the sample carrier shown in FIG. 4.

The carrier 1 comprises a circular plate 2 to which is fixed a peripheral ring 3. The latter is formed with two series of holes 4 and 5 forming two concentric circular rows. The angular pitch between the centers of the holes is constant about the entire periphery of the ring 3 and the centers of each pair of holes 4 and 5 are aligned radially.

Each hole furthermore has a horizontal shoulder 6, 7 (FIG. 2) to form a bearing surface for the containers R1 and R2 respectively. At its periphery, the plate 2 has holes 8 aligned radially with each pair of holes 4 and 5 and fitted with pourers 9, these pourers being arranged to cooperate with a discharge duct system (not shown) when they are located in the transvasation station C.

The transvasation station C also includes a post 10 supporting three cross-pieces 11a, 11b and 11c situated at different heights.

Figure 5:
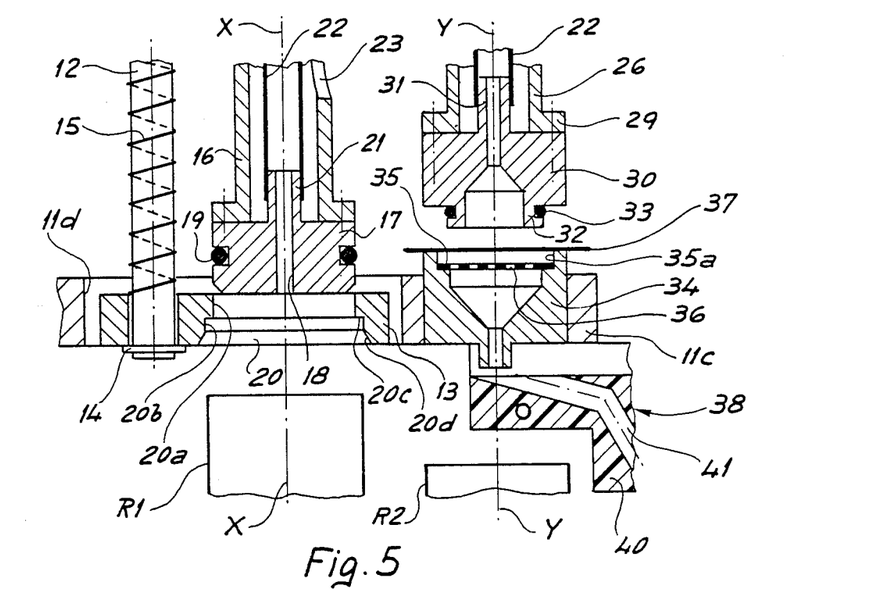
FIG. 5 is a view in cross-section and on an increased scale of certain details of this transvasation/metering station.

The upper cross-piece 11a supports four dounwardly-extending vertical stems 12 on which is slidably mounted a rectangular guide plate 13 held on these stems by retainer rings 14. Springs 15 are engaged over the stems between the cross-piece 11a and the guide plate 13 in order to bias the latter towards its lower position. When the guide plate 13 is in its lower position, it fits with considerable play in a rectangular opening 11d in the cross-piece 11c. Also, the stems 12 together with their springs 15 pass through holes 11e provided in the cross-piece 11b (Figs. 2 and 5).

A tube 16 is fixed vertically in the cross-pieces 11a and 11 b. At its lower end, it supports a piston 17 (FIG. 5) formed with a central passage 18 and surrounded by a gasket 19. The guide plate 13 has a stepped opening 20 with an upper cylindrical part 20a whose diameter is slightly greater than the diameter of the gasket 19 in its free state. The second part 20b of the opening 20 has a greater diameter so as to define a downwardly-facing radial shoulder 20c, the second part 20b joining with a downwardly-flaring part 20d of the opening 20.

The radial shoulder 20c serves as an abutment for the circular upper edge of the containers R1 during the metering process, as described below. The opening 20 is aligned with the axis X—X of the piston 17 and tube 16. The axis X—X intersects the circle 1a on which the container R1 are placed.

The piston 17 has on its upper face a nipple 21 to which is connected a communication tube 22 which passes through a lateral opening 23 in the tube 16.

The cross-piece 11b carries an electro-magnet 24 whose core (not shown) is coupled to a vertical rod 26 having a blind hole 27. The tube 22 penetrates this blind hole 27 through a lateral opening 28 in the rod 26. At its lower end, the rod 26 has a flange 29 to which is joined a connecting piece 30.

This piece is pierced through its center and has an upper nipple 31 to which is connected the tube 22, as well as a lower collar 32 about which is placed a gasket 33. The rod 26 and the connecting piece 30 form a vertically movable member controlled by the electromagnet 24.

Below this mobile member is provided a funnel-shaped piece 34 fixed in the cross-piece 11c and aligned vertically with the rod 26 and the connecting piece 30. The inlet of funnel-shaped piece 34 is formed with a radial shoulder 35 on which is placed a circular grid 36. The edge 35a of the radial shoulder 35 cooperates with the gasket 33 to ensure a fluidtight fit between the connecting piece 30 and the funnel-shaped piece 34 when the connecting piece 30 is in its lower position under the control of the electromagnet 24.

A band of filter paper 37 can travel between the funnel-shaped piece 34 and the connecting piece 30 when these members are spaced apart from one another.

Discharge means 38 are fixed under the cross-piece 11c. They comprise an electro-magnet 39 which is fixed in a U-shaped support 39a fixed to the cross-piece 11c and whose core is coupled to a sliding block 40. This block 40 is arranged beside the support 39a and has an internal duct 41 whose inlet can normally come to be placed below the outlet of funnel-shaped piece 34. The outlet of this duct 41 is connected to a discharge tube 42 which leads out above one of the pourers 9 of the plate 2. When the electro-magnet 39 is actuated, the block 40 moves back from in front of the funnel-shaped piece 34, so that the liquid flowing in this funnel will pour into the container R2 that is located in the transvasation or decanting station C at the time. The electro-magnet 24, the rod 26, the connecting piece 30 and the funnel-shaped piece 34 are aligned on the same vertical axis Y—Y which intersects the circle 1b of carrier 1, the points of intersection of the axes X—X and Y—Y respectively with the circles 1a and 1b being situated on common radii of these circles.

Figure 8:
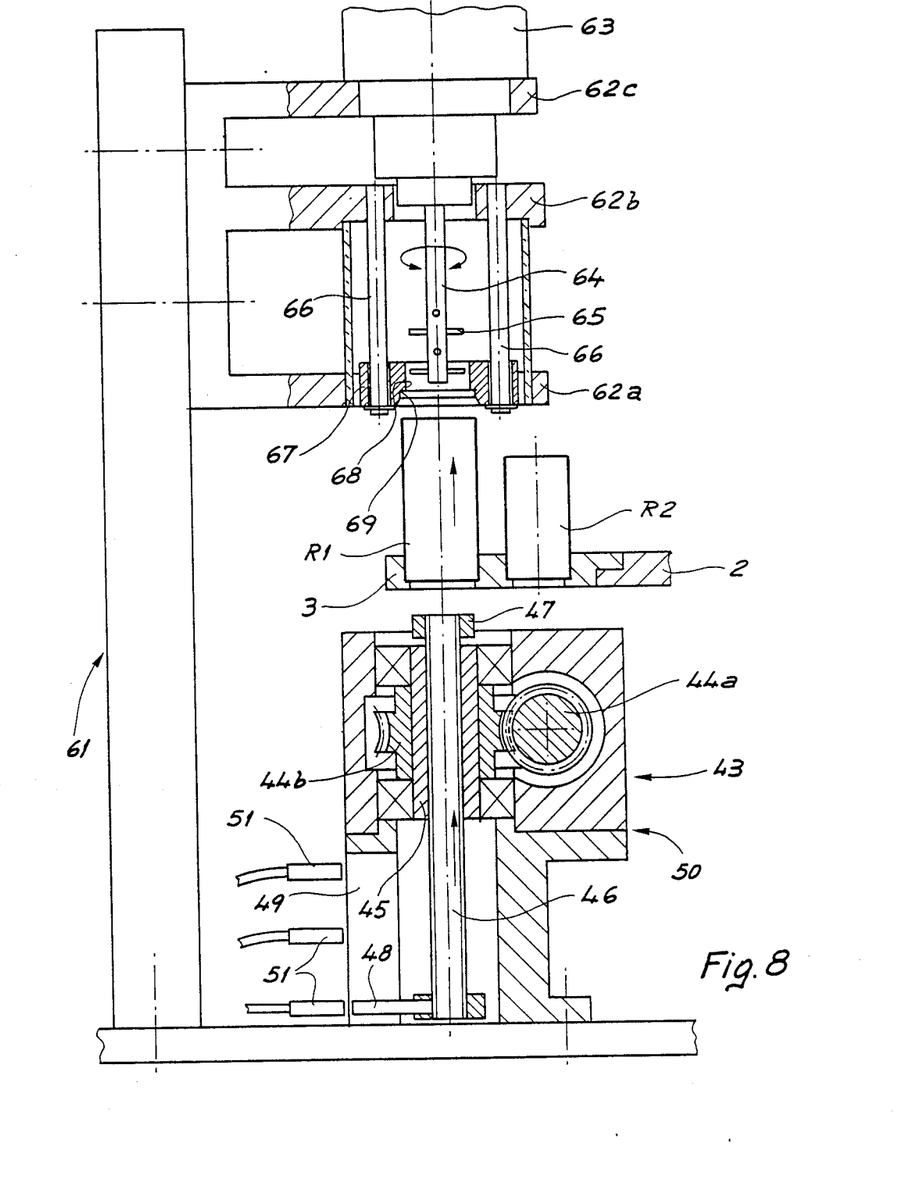
FIG. 8 is an elevational view, partly in cross-section, of a mixing station used in the apparatus shown in FIG. 1.

The transvasation/metering station C also comprises a lifting device 43 shown in its entirety in FIG. 8. This lifting device is provided in both the transvasation station C and in the mixing station B shown on FIG. 8. The lifting device comprises a horizontal endless screw 44a driven by an electric motor (not shown in the drawings). The endless screw 44a cooperates with a nut 44b that is solid with an internally threaded vertical sleeve 45 in which is vertically movable a threaded rod 46 provided at its upper end with a ring-shaped push-piece 47. This threaded rod 46 is prevented from rotating about its axis by means of a rotation-inhibiting pin 48 sliding in a slot 49 in the body 50 of the lifting device 43.

In the transvasation station C, the threaded rod 46 (FIG.2) is aligned along the axis X—X and will thus successively be aligned with all of the containers R1. Consequently, when the endless screw 44a is being rotatably driven in a given direction, the threaded rod 46 will lift the container R1 in station C, the push-piece 47 having a diameter slightly less than that of the corresponding hole 4 in the carrier 1.

During its upward movement, the edge of the container R1 engages the shoulder 20c, then the unit formed by the guide plate 13 and the container R1 continues its movement against the action of springs 15. During this movement, the piston 17 penetrates the container R1 and the gasket 19 acts as a fluidtight sealing segment. This opeation results in a reduction in the volume beneath the piston 17 thereby driving liquid out of the container R1 in a quanity proportional to the relative displacement of the piston and the container.

The liquid passes through the passage 18 of piston 17, the tube 22 and the connecting piece 30, and is discharged into the funnel-shaped piece 34.

When the direction of rotation of the screw 44a is reversed, the guide plate 13/container R1 unit moves down under the action of the springs 15 until the container R1 is again placed on the carrier 1.

Position detectors 51 (FIG. 8) are provided to detect the position of the threaded rod 46 and consequently of the container R1.

The detectors 51 are connected to the interface C1 to transmit information to the computer F which, from this information, generates control signals enabling coordination of the various movements carried out in the station C.

Hence, during a first lifting phase, i.e. when the pin 48 moves from the bottom detector 51 to the intermediate detector 51, the threaded rod 46 is driven at high speed. As soon as the pin 48 reaches the intermediate detector, the speed of the rod 46 is reduced and the electro-magnet 24 is controlled so as to apply the piece 30 against a portion of the band 37, which portion is in turn applied against and supported by the circular grid 36. Fluidtightness is provided by the gasket 33.

Figure 4:
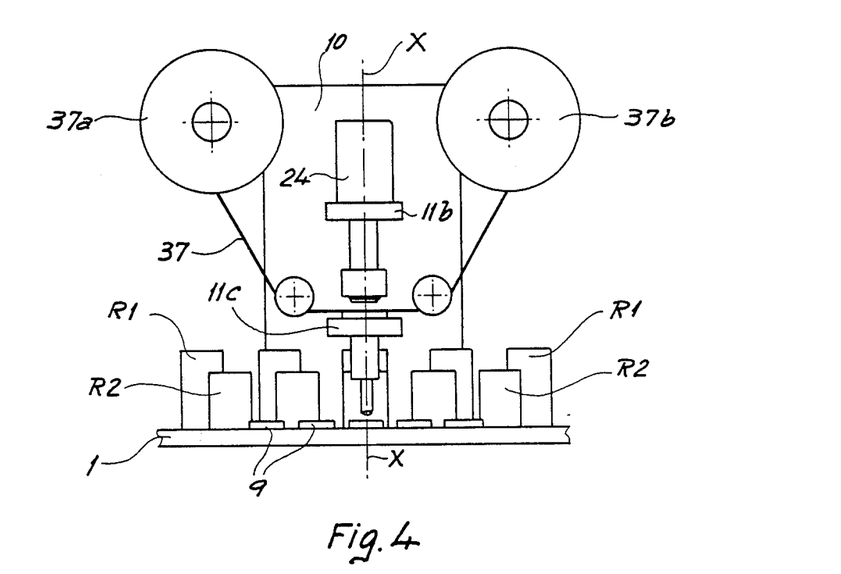
FIG. 4 is a front view, on a reduced scale, of the transvasation/metering station of FIG. 2.

FIG. 4 shows the band 37 being wound off a take-off spool 37a and wound on a take-up spool 37b driven by a motor (not shown). The latter is controlled by the computer F via the interface C1. Each transvasation or decanting operation is hence carried out with a fresh portion of the band 37. Driving of the band 37 is for example intermittent, in step with the carrier 1.

While the container R1 moves up, the liquid flows firstly in the duct 41 of block 40 and is discharged into the evacuation system through the pourer 9. When the pin 48 reaches the top detector 51, the electro-magnet 39 is controlled to withdraw the block 40 after which the liquid may flow into the container R2. The rotational movement of the screw 44a is then controlled by a numerical counter which precisely records the number of revolutions until a given number of revolutions is reached. During this time, the threaded rod 46 will have moved up by a very precise distance thereby determining the metering of the liquid since the piston will then have driven an exactly metered quantity of liquid from the container R1 into the container R2, whereas before withdrawal of the block 40 the liquid will have rinsed the entire flow path to eliminate any residue of the previously treated sample.

Figure 6:
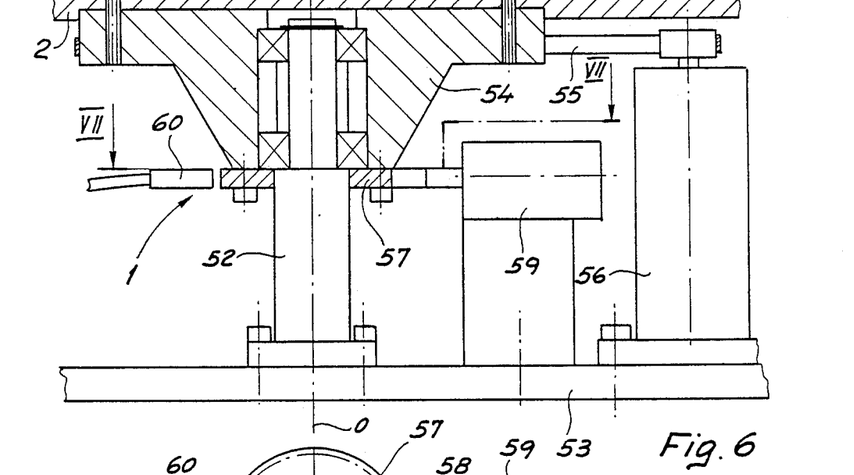
FIG. 6 is an elevational view, partly in cross-section, of a part of a rotary sample carrier used in the apparatus of FIG. 1.

FIGS. 6 and 7 show the arrangement of the plate 2. A pivoting shaft 52 is mounted vertically on the frame 53 of the apparatus. On the shaft 52 is mounted for rotation a wheel 54 to which the plate 2 is connected. Wheel 54 is connected by a belt 55 to a driving motor 56 fixed on the frame 53. Indexing of the positions of the plate 2 is provided by a toothed wheel 57 mounted below the wheel 54 about the pivoting shaft 52 and cooperating with a retractable locking member 58 controlled by an electro-magnet 59 with the aid of a detector 60.

FIG. 8 shows the mixing station B whose lifting device 43 has already been described. It comprises a post 61 with three cross-pieces 62a, 62b and 62c. An electric drive motor 63 is mounted on the cross-piece 62c and its output shaft is coupled to a rod 64 provided with mixing projections 65. This assembly rotates about a vertical axis. The cross-piece 62b supports two vertical slide stems 66 on which is slidably mounted a guide plate 67 having an opening 68 in which is provided a radial shoulder 69. Consequently, when the lifting device 43 of this mixing station is actuated, the container R1 located at that instant in this station is lifted and abuts by its upper edge against the radial shoulder 69. As a result of this, the guide plate 67 moves up and the rod 64 dips into the liquid in the container R1. An order is then given to the electric motor 63 to rotate the rod 64 to mix the liquid in the container R1.

When the direction of rotation of the endless screw 44a is reversed, the container R1 is moved back down on the carrier 1 and the guide plate 67 returns to its initial position. As in this instance the container R1 is not in fluid-tight contact with a gasket, contrary to what happens in the station C, the elements move down under the action of their own weight.

Figures 9, 10:
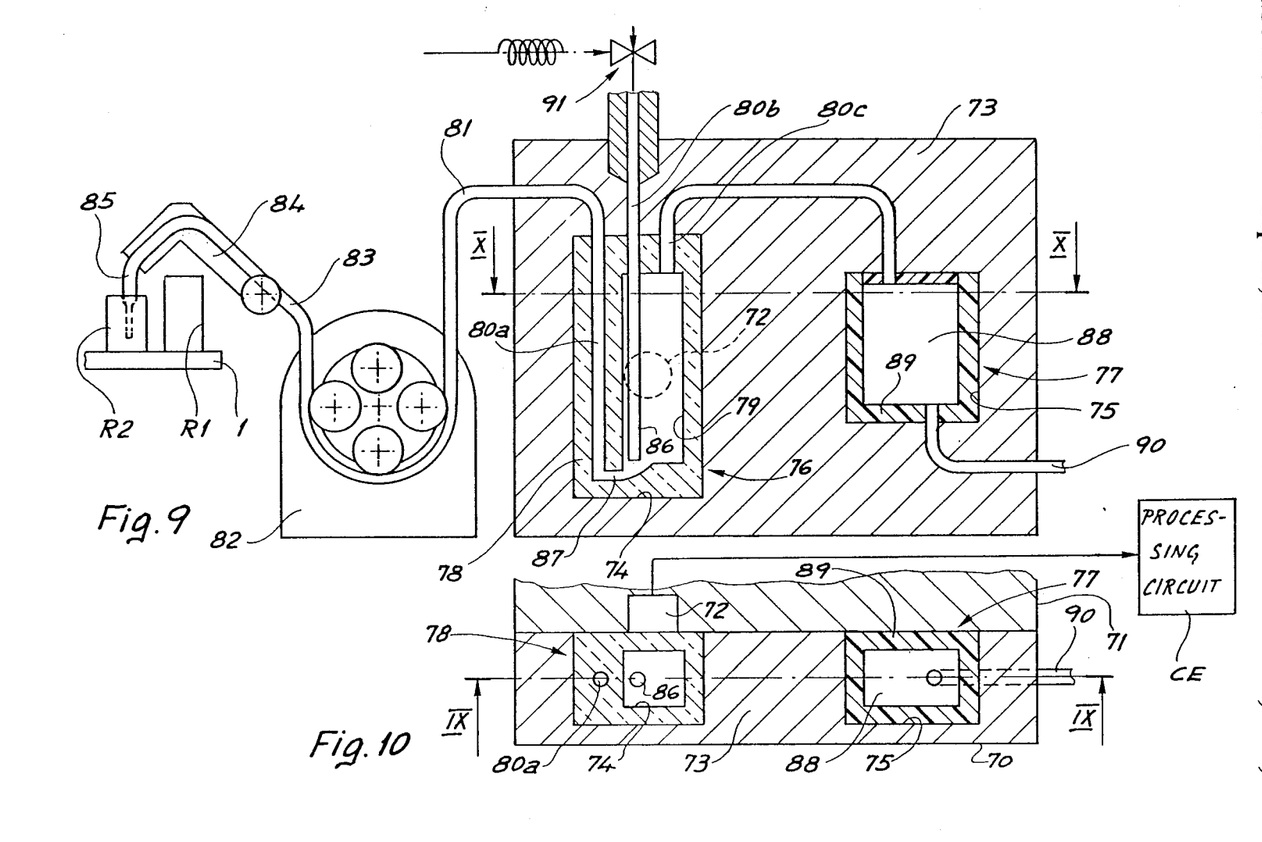
FIG. 9 is a schematic cross-section along line IX—IX of FIG. 10 of a photometric analysis station used in the apparatus of FIG. 1.
FIG. 10 is a cross-section along line X—X of FIG. 9.

As already indicated above, the apparatus described here as an example of the application of the invention comprises a bioluminescence measuring station E (FIG. 1) certain important details of which are shown on FIGS. 9 and 10.

The measuring station E comprises a measuring capsule 70 fixed to the front wall of a housing 71 containing a photomultiplier tube 72 and a processing circuit CE connected to this tube and able to provide a signal representing the quantity of light sensed by the tube during each processing cycle of a sample. The housing may be that sold under the reference XP-2000 by Skan AG, of 4009 Basel-Alschwil, Switzerland.

The measuring capsule 70 comprises a rigid metal plate 73 screwed to the housing 71 in a manner ensuring light-tightness. The plate 73 has two cavities 74 and 75 in which are lodged respectively a measuring cell 76 and a cell 77 for the removal of the analysed sample.

The measuring cell 76 is formed of a hollow block 78 of transparent material defining a chamber 79. Three ducts 80a, 80b and 80c lead into this chamber 79. The duct 80a is provided directly in the hollow block 78 and communicates via a tube 81 with a peristaltic pump 82. The peristaltic pump 82 is connected by a tube 83 to a pivoting arm 84 which supports a pipette 85. The arm 84 pivots on a fixed support (not shown) mounted on the frame 53 of the apparatus. Hence the pipette 85 can dip into each container R2 to aspirate its sample, as a result of the coordinated movements of the arm 84 and the carrier 1 under the control of the computer F.

The duct 80b communicates with a tube end 86 which extends down into the chamber 79 with its open end near the end of the duct 80a.

As may be seen from FIG. 9, the end wall of chamber 79 has a turbulence recess 87.

The duct 80c is provided in the body of the rigid plate 73 and leads into a non-return chamber 88 provided in a hollow body 89 lodged in the cavity 75 of the plate. The non-return chamber 88 is connected to the evacuation system via a duct 90 in the plate.

The peristaltic pump 82 is reversible in order to allow evacuation of the measuring chamber 79.

The duct 80b serves the purpose of adding an enzyme to the sample to produce therein the bioluminescence reaction. To control this addition, the duct 80b is connected to a valve 91 controlled by the computer F via the interface E1 (FIG. 1). The valve 91 is in turn connected to a reservoir of an enzymatic substance (not shown).

The bioluminescence reaction requires only a very small quantity of liquid sample, much less than the quantity contained in the containers R2. It is hence possible, here also, to use the sample itself to remove, from the flow circuit and the measuring cell, residues of the previously analysed sample. The flushing time needed for adequate rinsing of this circuit may easily be determined as it corresponds to a given time of operation of the peristaltic pump 82. It hence suffices to start introducing the enzyme into the measuring cell at a predetermined instant at the end of this operating time to be certain that the measurement does indeed take place on a sample that is not polluted by the previous sample. In other words, the valve 91 must be open at this instant while the pump continues to operate for a given period of time. This causes, by virtue of the turbulence recess 87 situated in the neighborhood of the tube end 86, an intimate mixture of the sample and the enzyme. The excess liquid is evacuated through the non-return chamber 88.

The reaction of the enzyme with the sample produces in the liquid contained in the measuring chamber 79 the very abrupt appearance of a certain quantity of light that is dependent on the quantity of ATP released in the sample. This quantity of light is measured by the photomultiplier tube 72 which generates a measurement signal processed in the circuit CE. The latter transmits the thus-obtained data to the computer F via the interface E1.

Figure 11:
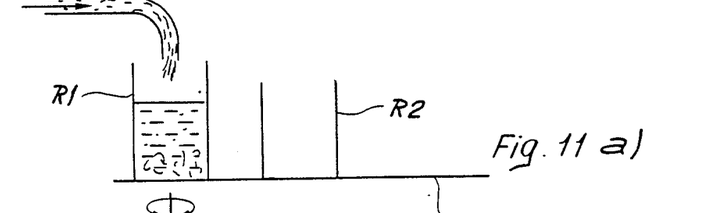
FIGS. 11a–11f are explanatory diagrams illustrating the operation of the apparatus shown in FIG. 1.

FIG. 11 schematically illustrates steps $a$ through $f$ of the overall operation of the just-described apparatus.

The carrier 1 is driven with a step-by-step rotary motion so that the pairs of containers R1 and R2 are successively placed in the work stations A to E grouped about the carrier 1. These stations operate simultaneously on five samples at a time.

Step $a$ consists in pouring into the container R1 a certain quantity of acid (for example $H_2SO_4$) capable of releasing ATP from the cells contained in the material to be analysed. This material is previously put into the containers R1 outside the apparatus, possibly with additives in accordance with the methodology described in the aforementioned article and patent application.

Step $b$ consists in mechanically accelerating the release of ATP, with the containers R1 being moved vertically as described above.

Step $c$ is carried out in station C and consists in the transvasation/metering operation that makes up the essence of the invention. During this operation, a precisely metered quantity of the mixture resulting from the mixing operation is transferred into the container R2.

During step $d$, the pH of this metered quantity of the sample is adjusted so as to be very close to that of a neutral solution.

Figure 11E:
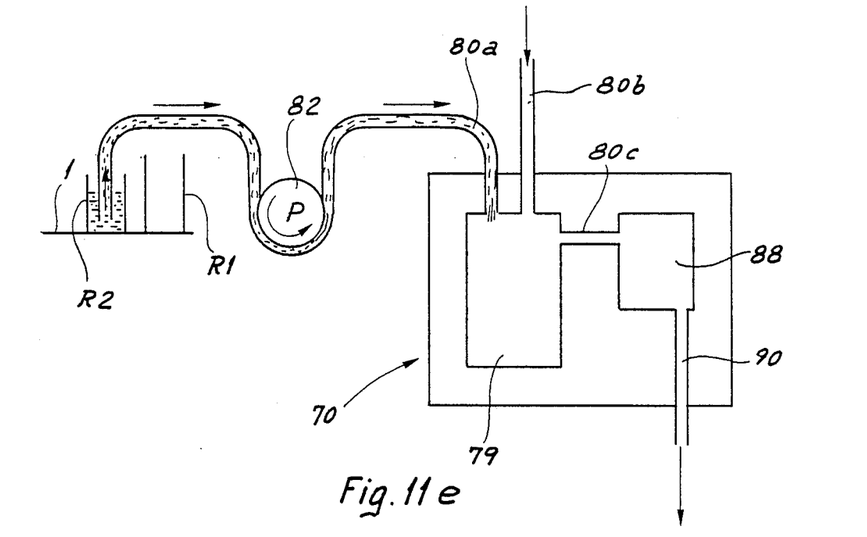

Step $e$ consists in the bioluminescence measurement as such and as previously described with reference to FIGS. 9 and 10. Here, the pump is so driven that it feeds the liquid of the container R2 towards the measuring cell.

Figure 11F:
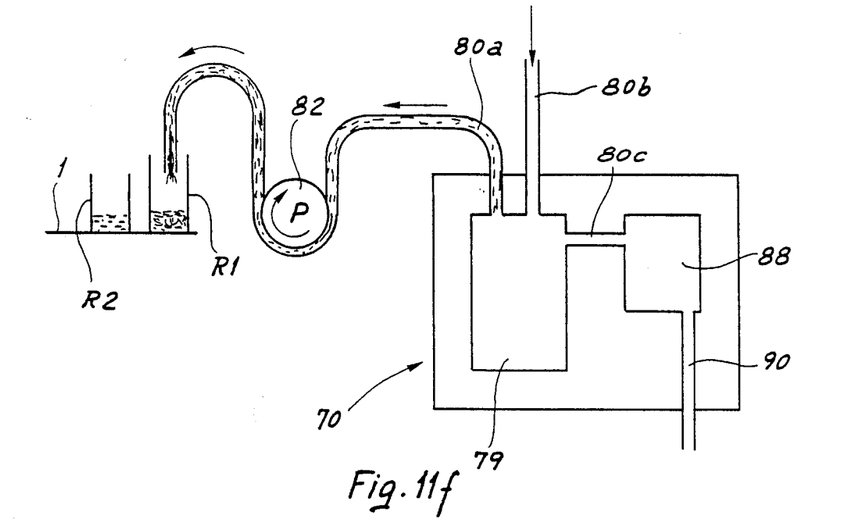

And step $f$ consists in driving the liquid remaining in the measuring capsule 70 after the measurement, into the container R1 with the arm 84 placed so that the pipette is located above the latter.

We claim:

1. Apparatus for metering liquid samples comprising a plurality of pairs of first and second containers, the first containers each being adapted to contain a sample to be metered plus a quantity in excess of the volume to be obtained, the second containers being adaped to receive the metered quantities of sample, a station for decanting successive samples from their first container into their second container, this decanting station comprising means for pumping sample to carry out the decanting, a pouring assembly adapted to communicate with the second containers and selective descharge means adapted to be selectively positioned between the pouring assembly and each second container during a predetermined period of time at the beginning of the decanting and be withdrawn during the remainder of the decanting, said predetermined period of time corresponding at most to the decanting of the excess quantity of the sample, and transport means for successively bringing each pair of first and second containers into the decanting station.

2. Apparatus according to claim 1, wherein said pumping means comprise a piston cooperating with each of said first containers to form therewith a cylinder-piston unit, and drive means for producing a relative axial movement between said piston and each of said first containers during transvasation decanting.

3. Apparatus according to claim 2, wherein said piston is fixedly mounted in said decanting station and said drive means comprise a vertically movable push piece able to engage said first container over said piston by pushing against the bottom of said first container, then to cause the piston to penetrate in said first container a predetermined distance, and means being provided for disengaging the first container from the piston after completion of the decanting.

4. Apparatus according to claim 3, wherein the disengaging means comprise a guide plate movable along vertical guides provided in said decanting station, said plate having an opening for the passage of the piston, said opening being bordered by a shoulder against which the upper edge of the first container comes to abut during said relative movement of the piston and the first container, and wherein said disengaging means comprise springs associated with said guides and acting on said plate against upward movement thereof.

5. Apparatus according to claim 2, 3 or 4, wherein said piston comprises a central passage through which each sample is driven out of its first container during decanting.

6. Apparatus according to claim 1, wherein filtering means are associated with said pouring assembly for filtering each sample driven out of its first container during decanting.

7. Apparatus according to claim 6, wherein said pouring assembly comprises a first, funnel-shaped piece below which are successively brought said second containers, and a second piece movably mounted in relation to the first piece and fitting in a fluidtight manner in the inlet of the first piece with said interposed filtering means, a second piece communicating with a cylinder-piston sub-unit of the means for pumping to deliver the liquid being decanted into said funnel-shaped first piece.

8. Apparatus according to claim 7, wherein said filtering means form part of a band of filter paper brought step-by-step into said pouring assembly to renew the filter paper after each decanting operation.

9. Apparatus according to claim 1, wherein said pouring assembly comprise a mobile unit with an internal duct which communicates with an evacuation means and wherein said mobile unit is slidably mounted in said decanting station so that the mouth of said duct may be placed under said pouring assembly while said excess quantity of the sample is driven out of said first container.

10. A method of metering liquid samples comprising the steps of:
providing a plurality of pairs of first and second containers;
introducing into each of the first containers a sample to be metered plus a sample quantity in excess of the volume to be obtained;
decanting in a decanting station successive samples by pumping them from their first container into their second container;
providing a pouring assembly adapted to communicate with the second container;
selectively positioning a selective discharge means between the pouring assembly and each second container during a predetermined period of time at the beginning of the decanting, and withdrawing the selective discharge means during the remainder of the decanting, said predetermined period of time corresponding at most to the decanting of the excess quantity of the sample; and
successively bringing each pair of first and second containers into the decanting station.

* * * * *